United States Patent
Matsuda

(10) Patent No.: US 6,617,598 B1
(45) Date of Patent: Sep. 9, 2003

(54) CHARGED PARTICLE BEAM IRRADIATION APPARATUS

(75) Inventor: Koji Matsuda, Hitachi (JP)

(73) Assignee: Hitachi, Ltd., Tokyo (JP)

(*) Notice: Subject to any disclaimer, the term of this patent is extended or adjusted under 35 U.S.C. 154(b) by 0 days.

(21) Appl. No.: 10/253,488

(22) Filed: Sep. 25, 2002

(30) Foreign Application Priority Data

Feb. 28, 2002 (JP) .................................... 2002-052563

(51) Int. Cl.⁷ ................................................. G21G 5/00

(52) U.S. Cl. ................. 250/492.3; 250/398; 250/505.1; 315/501; 315/505

(58) Field of Search .............................. 250/398, 492.3, 250/505.1; 315/501, 505

(56) References Cited

U.S. PATENT DOCUMENTS 6,316,776 B1 * 11/2001 Hiramoto et al. .......... 250/492.3
2002/0090194 A1 * 7/2002 Tajima ...................... 385/147

FOREIGN PATENT DOCUMENTS

| JP | 10151211 A | * | 6/1998 | ............ A61N/5/10 |
| JP | 10314324 A | * | 12/1998 | ............ A61N/5/10 |
| JP | 2000202048 A | * | 7/2000 | ............ A61N/5/10 |

OTHER PUBLICATIONS

Review of Scientific Instruments, vol. 64 No. 8 (Aug. 1993), pp 2055–2122.*
Physics and Medical Biology, vol. 44 (1999), pp. 2765–2775.*

* cited by examiner

Primary Examiner—John R. Lee
Assistant Examiner—Erin-Michael Gill
(74) Attorney, Agent, or Firm—Dickstein Shapiro Morin & Oshinsky LLP

(57) ABSTRACT

An charged particle beam irradiation apparatus is provided which increases the width in a depth direction of a Bragg peak to be formed, by means of a simple construction. The charged particle beam irradiation apparatus includes a charged particle beam generation device and an irradiation field forming device. The charged particle beam generation device has a front accelerator and a synchrotron. An ion beam is guided to the irradiation field forming device from the synchrotron. The irradiation field forming device has a beam enlarging device, a Bragg peak enlarging device and a ridge filter. A pair of filter elements which constitute the Bragg peak enlarging device have a plurality of stick-shaped portions spaced apart from one another. The filter elements are disposed with their respective stick-shaped portions partly superposed to extend in mutually different directions. An ion beam that has passed through the Bragg peak enlarging device contains three ion beam components having different energies produced according to the difference between passed positions of each of the filter elements, whereby the width of a Bragg peak formed in the body of a patient is increased.

13 Claims, 5 Drawing Sheets

CHARGED PARTICLE BEAM IRRADIATION APPARATUS

BACKGROUND OF THE INVENTION

1. Field of the Invention

The present invention relates to a charged particle beam irradiation apparatus, and more particularly, to a charged particle beam irradiation apparatus having an accelerator.

2. Background Art

A charged particle beam (hereinafter referred to as an ion beam) which is ejected from a charged particle beam generation device such as an accelerator is a thin beam. The ion beam is enlarged (or scanned) in a plane perpendicular to the advancing direction of the ion beam by an irradiation field forming device in order to irradiate uniformly a cancerous tumor which is an irradiation target portion. The ion beam ejected from the charged particle beam generation device is in general a beam having a uniform energy. When this charged particle beam, particularly a proton beam and a heavy particle beam, are irradiated onto an irradiation target portion, a radiation dose distribution having a peak at a particular depth determined by their energies is formed. The peak of the radiation dose distribution is called Bragg peak. Since the spread of the Bragg peak is as narrow as several mms, the ion beam is enlarged by the irradiation field forming device so that the irradiation target portion is uniformly irradiated.

In addition, to irradiate uniformly the irradiation target portion with an ion beam, it is preferable that a plurality of ion beams having different energies be added together with their weights made mutually different. As described in *Review of Scientific Instruments*, Vol. 64, No. 8 (August 1993), pp. 2055–2122, there are known methods for enlarging an energy distribution, such as (1) a method of directly changing the energy of an ion beam from an accelerator (energy scanning) and (2) a method of passing an ion beam through a part of a rotating disk-shaped plate having an appropriately distributed thickness (range modulating propeller) as well as a method of disposing a wedge-shaped structure having an appropriately distributed thickness in an area through which an ion beam is to pass.

An energy distribution enlarging device using the energy scanning can impart a desired distribution to the total energy distribution of an ion beam to be irradiated onto an irradiation target portion, by appropriate control of an energy to be given to the ion beam from a radio-frequency accelerating cavity of an accelerator and by appropriate control of the amount of irradiation with the ion beam having the energy. An energy distribution enlarging device using the range modulating propeller (or the ridge filter) can impart a desired distribution to the energy distribution of a passing ion beam by setting to a desired distribution the distribution of the thickness of a portion through which an ion beam is to pass.

In addition, a method of widening an energy distribution to a Gaussian distribution in a narrow range compared to the spread of an irradiation target portion is described in Physics and Medical Biology, Vol. 44 (1999), pp. 2765–2775.

Japanese Patent Laid-Open No. 314324/1998 describes a ridge filter constructed by stacking a multiplicity of plates each having a width which becomes narrower toward its top. The ridge filter can be easily manufactured owing to such construction.

SUMMARY OF THE INVENTION

As the thickness of an irradiation target portion in the advancing direction of an ion beam becomes larger, the energy distribution required to irradiate the irradiation target portion with the ion beam becomes wider. In addition, as the depth of an irradiation target portion in the advancing direction of an ion beam becomes shallower, the spread of a Bragg peak becomes narrower, and therefore, the energy distribution of the ion beam needs to be made finer so that the ion beam can be uniformly irradiated onto the irradiation target portion. In either case, as described previously, if ion beams having different energies and weights are to be added together, a multiplicity of such ion beams need to be generated.

The ridge filter described in Japanese Patent Laid-Open No. 314324/1998 is capable of obtaining ion beam components having different energies by a number corresponding to the number of plates stacked in the advancing direction of the ion beam.

The invention aims to provide a charged particle beam irradiation apparatus capable of increasing the width in a depth direction of a Bragg peak to be formed, by means of a simple construction.

Therefore, according to the invention, a Bragg peak enlarging device for increasing the width in a depth direction of a Bragg peak formed by a charged particle beam scanned by a charged particle beam scanning device is provided with a first filter member and a second filter member which are disposed in order in an advancing direction of the charged particle beam and each of which has at least one thick-walled portion in a direction intersecting the advancing direction. The first filter member and the second filter member are disposed with their respective thick-walled portions intersecting mutually in the advancing direction of the charged particle beam.

Since the first filter member and the second filter member are disposed with their respective thick-walled portions intersecting mutually in the advancing direction of the charged particle beam, a plurality of charge particle beam components having different energies can be obtained by means of a simple structure. It is possible to increase to a further extent the width in a depth direction of a Bragg peak formed in the body of a patient by irradiation with a charged particle beam having such charge particle beam components. Such an increase in the width of the Bragg peak leads to a reduction in treatment time. In addition, in the case where a ridge filter is used, the ridge filter can be easily manufactured.

A first filter member and a second filter member which is provided with a thick-walled portion different in thickness in the advancing direction of a charged particle beam from the thickness of the thick-walled portion of the first filter member may be disposed with their respective thick-walled portions partly intersecting mutually in the advancing direction of the charged particle beam. In this case as well, the width in the depth direction of a Bragg peak to be formed can be increased by the above-described simple structure. In particular, the respective thick-walled portions of the first filter member and the second filter member are made mutually different in thickness in the advancing direction of the charged particle beam, and the first filter member and the second filter member are disposed with their respective thick-walled portions partly intersecting mutually in the advancing direction of the charged particle beam. Accordingly, it is possible to obtain charged particle beam components having different energies by a number larger than the number of the thick-walled portions different in thickness in the advancing direction of the charged particle beam. Accordingly, it is possible to obtain far more ion beam components having different energies by means of a simple construction in which fewer members are disposed in the advancing direction of the charged particle beam, whereby it is possible to increase the width of a Bragg peak in the depth direction.

Preferably, in the case where an affected part is divided into a plurality of irradiation target layers in its depth direction and a charged particle beam is irradiated onto each of the irradiation target layers by using a charged particle beam deflecting device or a charged particle beam enlarging device, an increase in the width of the Bragg peak can increase the thickness of each of the irradiation target layers and can decrease the number of energies to be changed.

Preferably, a Bragg peak enlarging device has a construction in which a plurality of filter elements are superposed on each other so that stick-shaped portions provided in the respective filter elements are arranged in mutually different directions, or a construction in which a plurality of filter elements are superposed on each other so that thick-walled portions provided in the respective filter elements are arranged in mutually different directions. This construction simplifies the construction of the Bragg peak enlarging device.

BRIEF DESCRIPTION OF THE DRAWINGS

The invention will become more readily appreciated and understood from the following detailed description of preferred embodiments of the invention when taken in conjunction with the accompanying drawings, in which.

DETAILED DESCRIPTION OF THE INVENTION

Embodiment 1

Figure 1:
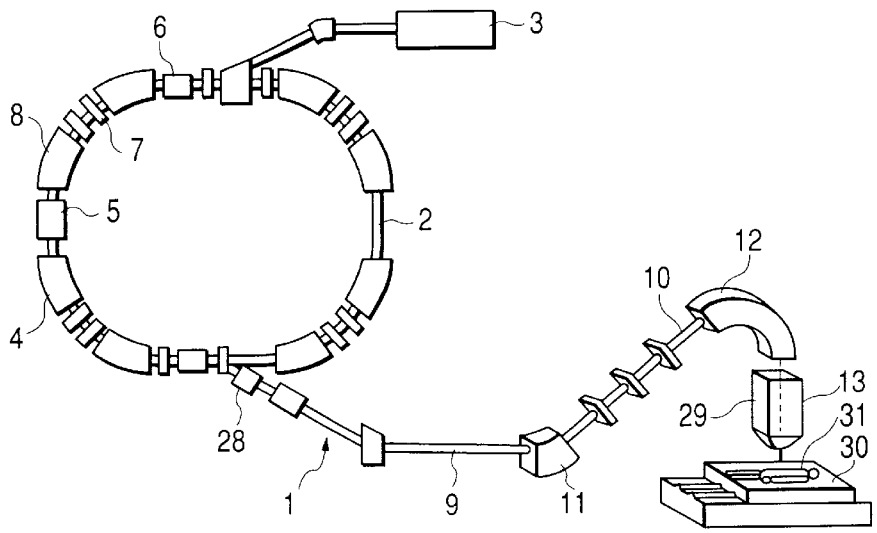
FIG. 1 is a diagrammatic view of the construction of a charged particle beam irradiation apparatus according to one preferred embodiment of the invention.

A charged particle beam irradiation apparatus according to a first preferred embodiment of the invention will be described below with reference to FIG. 1. A charged particle beam irradiation apparatus according to the first preferred embodiment includes a charged particle beam generation device 2 and an irradiation field forming device 13. The charged particle beam generation device 2 has an ion source (not shown), a front accelerator 3 and a synchrotron 4. Ions (for example, cations (or carbon ions)) generated by the ion source are accelerated by the front accelerator (for example, a linear accelerator) 3. An ion beam ejected from the front accelerator 3 is injected into the synchrotron 4. In the synchrotron 4, this ion beam is accelerated by energy given to the ion beam by radio-frequency electric power applied from a radio-frequency accelerating cavity 5.

After the energy of the ion beam circling in the synchrotron 4 has been increased to a preset energy level, a radio-frequency wave is applied to the ion beam from an ejecting radio-frequency applying device 6. The ion beam circulating within its stability limits is shifted outside the stability limits by the application of the radio-frequency wave, and is ejected from the synchrotron 4 through an ejecting deflector 28. During the ejection of the ion beam, currents guided to electromagnets such as four-pole electromagnets 7 and deflection electromagnets 8 provided in the synchrotron 4 are respectively kept at preset values, and the stability limits are also kept approximately constant. When the application of radio-frequency electric power to the radio-frequency applying device 6 is brought to a stop, the ejection of the ion beam from the synchrotron 4 comes to a stop.

The ion beam ejected from the synchrotron 4 reaches an irradiation field forming device 13 via a beam transportation line 9. An inverse U-shaped part 10 which is a part of the beam transportation line 9 and the irradiation field forming device 13 are disposed on a rotatable gantry (not shown). The inverse U-shaped part 10 has deflection electromagnets 11 and 12.

Figure 2:
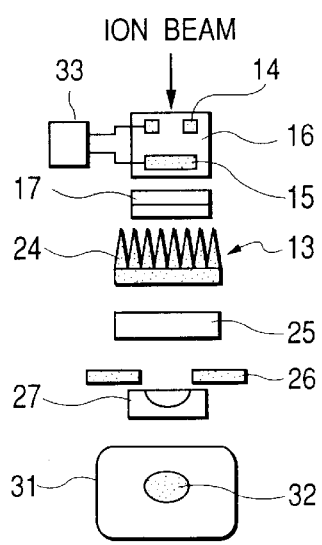
FIG. 2 is a detailed view of the construction of the irradiation field forming device shown in FIG. 1.

The irradiation field forming device 13 includes a casing 29 in which a beam enlarging device 16 having a pair of scanning electromagnets 14 and 15, a Bragg peak enlarging device 17, a ridge filter 24 and a range shifter 25 are disposed as shown in FIG. 2. The beam enlarging device 16, the Bragg peak enlarging device 17, the ridge filter 24 and the range shifter 25 are disposed in that order from an upstream side to a downstream side in the advancing direction of the ion beam. Although not shown, the beam enlarging device 16 is provided with a scatter under the scanning electromagnet 15. The scatter is made of lead or tungsten. The irradiation field forming device 13 can be fitted with a collimator 26 and a bolus 27 which are to be prepared for each patient who is radiated with an ion beam. The range shifter 25 has the function of shifting the distribution of energy of the ion beam in the body in the depth direction thereof. The Bragg peak enlarging device 17 may be disposed in the rear of the ridge filter 24.

Figure 3:
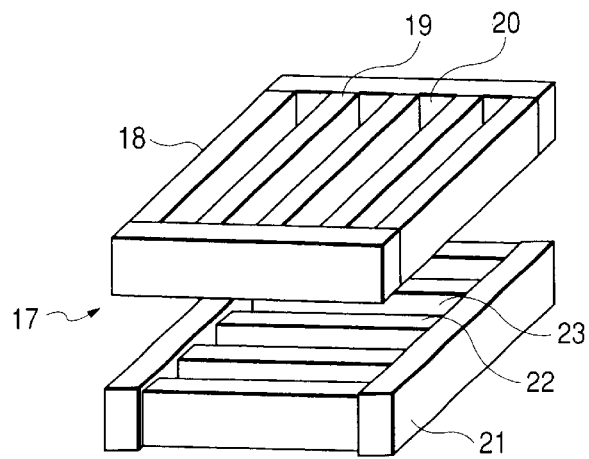
FIG. 3 is a perspective view of the Bragg peak enlarging device shown in FIG. 2.

As schematically shown in FIG. 3, the Bragg peak enlarging device 17 has a pair of filter elements 18 and 21. The filter element 18 is provided with a plurality of stick-shaped portions 19 which form hole portions 20 thereamong. The filter element 18 has a construction in which the stick-shaped portions 19 are connected to one another at their opposite ends with gaps formed between each of the stick-shaped portions 19. In other words, it can also be said that the filter element 18 is made of a plate in which a plurality of elongated through-holes (the hole portions 20) are formed. Similarly to the filter element 18, the filter element 21 is provided with a plurality of stick-shaped portions 22 which form hole portions 23 thereamong, and has a construction in which the stick-shaped portions 22 are connected to one another at their opposite ends. Each of the stick-shaped portions 19 and 22 is a thick-walled portion. Each of the stick-shaped portions 19 and 22 has a horizontal thickness of 1 mm, and the stick-shaped portions 19 are spaced 1 mm apart from one another and the stick-shaped portions 22 are also spaced 1 mm apart from one another. Each of the stick-shaped portions 19 and 22 has a rectangular cross-sectional shape. The filter element 18 is disposed over the filter element 21. The filter element 18 and the filter element 21 are disposed with the stick-shaped portions 19 and the stick-shaped portions 22 arranged in directions which differ from each other (in directions which differ 90° from each other). Specifically, in the first embodiment, the filter element 18 and the filter element 21 are disposed so that the stick-shaped portions 19 and the stick-shaped portions 22 mutually intersect, more particularly, cross at right angles as viewed from above. The horizontal shape of each of the filter elements 18 and 21 is a square with sides of about 25 cm.

A patient 31 having a malignant tumor-affected part to be irradiated with an ion beam is positioned on a treatment table under the irradiation field forming device 13. At this time, the collimator 26 and the bolus 27 for the patient 31 are already disposed below the range shifter 25 in the irradiation field forming device 13. After the positioning of the patient 31 has been completed, an ion beam having preset energy, as described above, is ejected from the synchrotron 4 of the charged particle beam generation device 2 and reaches the irradiation field forming device 13 through the inverse U-shaped part 10. Currents are supplied from a power source unit 33 to the respective electromagnets 14 and 15 of the beam enlarging device 16. The electromagnet 14 moves the position of the ion beam in a horizontal plane in the X-axis direction thereof. The electromagnet 15 moves the position of the ion beam in the horizontal plane in the Y-axis direction perpendicular to the X axis. In the first embodiment, the scanning electromagnets 14 and 15 are used to move the ion beam so that the ion beam circle at a certain radius in the horizontal plane. The scanning electromagnets 14 and 15 function as a charged particle beam scanning device which circles the ion beam. The circled ion beam is enlarged by the function of the aforementioned scatter in directions perpendicular to the direction in which the ion beam is injected into the beam enlarging device 16. This enlarged ion beam reaches the Bragg peak enlarging device 17.

Figure 4:
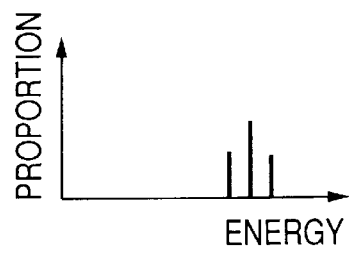
FIG. 4 is an explanatory view showing the energy distribution of an ion beam that has passed through the Bragg peak enlarging device.
Figure 5:
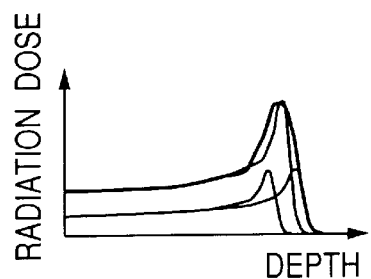
FIG. 5 is an explanatory view showing the distribution of radiation dose in an affected part on the basis of irradiation with the ion beam that has passed through the Bragg peak enlarging device.

The Bragg peak enlarging device 17 decreases the energy of a part of the passing ion beam. Specifically, an ion beam passing through the stick-shaped portions 19 of the filter element 18 decreases its energy. An ion beam passing through the hole portions 20 of the filter element 18 does not decrease its energy. In the next filter element 21, an ion beam passing through the stick-shaped portions 22 decreases its energy. An ion beam passing through the hole portions 23 does not decrease its energy. In this manner, the stick-shaped portions 19 and 22 attenuate the energy of the ion beam. The ion beam that has passed through the Bragg peak enlarging device 17 contains a first ion beam component that has passed through a portion where the stick-shaped portions 19 and 22 of the two filter elements 18 and 21 are superposed on each other, a second ion beam component that has passed through the stick-shaped portions 19 or 22 of one of the two filter elements 18 and 21, and a third ion beam component that has passed through the hole portions 20 and 23 of the two filter elements 18 and 21. Because the stick-shaped portions 19 and 22 are the same in thickness, the ion beam that has passed through the Bragg peak enlarging device 17 is separated into the three ion beam components having different energies as shown in FIG. 4. The first ion beam component, because it passes through the stick-shaped portions 19 and 22 in the vertical direction, is large in the width of energy decrease, and has the smallest energy. The energies of the respective ion beam components increase in the order of the first ion beam component, the second ion beam component and the third ion beam component. The distribution of radiation dose in the body of the patient 31 in the case of direct irradiation of the affected part of the patient 31 with the ion beam that has passed through the Bragg peak enlarging device 17 is as shown in FIG. 5. Namely, the width of the Bragg peak of the ion beam is increased by the superposition of the three ion beam components. As described above, the Bragg peak enlarging device 17 has the function of increasing the width of the Bragg peak in a depth direction from the surface of the body of the patient 31.

Figure 6A:
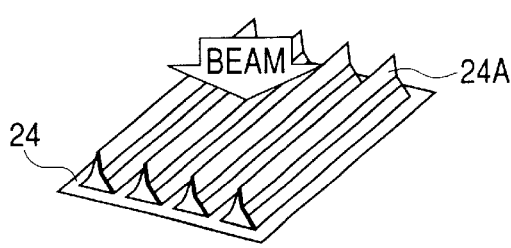
FIGS. 6A and 6B show the construction of a ridge filter, FIG. 6A being a perspective view of the ridge filter and FIG. 6B being a partly enlarged view of a longitudinal sectional shape of the ridge filter.
Figure 6B:
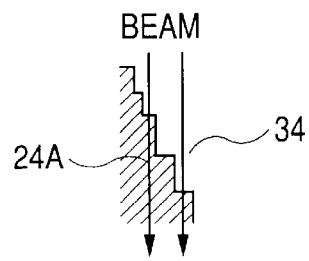

The ion beam that has passed through the Bragg peak enlarging device 17 reaches the ridge filter 24. As shown in FIG. 6A, the ridge filter 24 is constructed so that a plurality of filter elements (wedge-shaped elements) 24A each having a wedge-like shape in cross section are arranged in parallel with one another. The filter elements 24A are arranged at a pitch of about 1 cm. As shown in FIG. 6B, each of the filter elements 24A has a multiplicity of steps 34 formed on the surface of each of two sides except its bottom side. The ion beam that has passed through the ridge filter 24 contains, owing to the plurality of filter elements 24A on which the multiplicity of steps 34 are formed, a multiplicity of ion beam components having different energies according to the thicknesses of different portions of each of the filter elements 24A through which the ion beam has passed, that is to say, ion beam components having different energies by the number of the steps 34 of each of the filter elements 24A. Accordingly, different Bragg peaks can be formed by the number of the steps 34 at different positions in the depth direction in the body of the patient 31.

Figure 7:
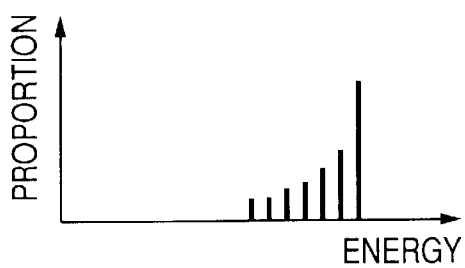
FIG. 7 is an explanatory view showing the energy distribution of an ion beam that has passed through the ridge filter.
Figure 8:
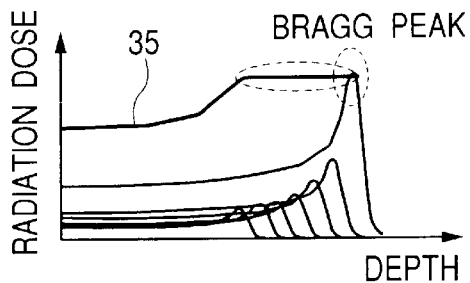
FIG. 8 is an explanatory view showing the distribution of radiation dose in an affected part on the basis of irradiation with an ion beam that has passed through the ridge filter.

In a related art irradiation field forming device in which the Bragg peak enlarging device 17 is not disposed, for example, over twenty steps are formed on one surface of each wedge-shaped element of its ridge filter. In this case, an ion beam that has passed through the ridge filter contains over twenty ion beam components having different energies. The distribution of the number of ions against energy is determined by the proportion occupied in a wedge-shaped element by each step that determines the energy of ions. Accordingly, the energy distribution of the ion beam that has passed through the ridge filter is determined by the cross-sectional shape of the wedge-shaped element. FIG. 7 shows the energy distribution of an ion beam that has passed through a ridge filter having seven steps formed on one surface in the related art irradiation field forming device in which the Bragg peak enlarging device 17 is not disposed. A depth to be reached by an ion beam in the body is determined by the energy of the ion beam. An ion beam having larger energy reaches a deeper position, whereas a position to be reached by an ion beam having smaller energy becomes shallower. In the case where a patient is irradiated with the ion beam containing seven ion beam components having different energies as shown in FIG. 7, different Bragg peaks are formed at different seven positions reached in the body by the respective ion beam components according to the energies thereof. When the patient is irradiated with such ion beam, the total distribution of radiation doses against the depth direction in the body is as shown by a line 35 in FIG. 8, because the Bragg peaks are added together. Namely, a region which is high and uniform in radiation dose is spread in the depth direction. In FIG. 8, the distribution of radiation dose shown by each thin line is the distribution of radiation dose against each ion beam component that has passed through any one of the steps of the wedge-shaped element. The energy of an ion beam to be ejected from, for example, the synchrotron 4 is adjusted so that the region which is uniform in radiation dose is positioned at the affected part of the patient.

Figure 9:
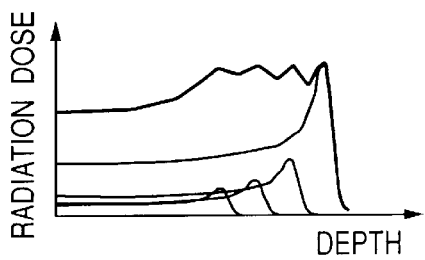
FIG. 9 is an explanatory view showing the distribution of radiation dose in an affected part on the basis of irradiation with an ion beam that has passed through a ridge filter worked with low precision.

If the number of steps to be formed on each wedge-shaped element of a ridge filter is decreased and the interval of the steps is made coarse in the height direction, the fabrication of the ridge filter is easy. However, ion beam components having different energies, which are contained in an ion beam that has passed through the ridge filter, are decreased in number and the difference in energy between the ion beam components increases, so that the distribution of radiation dose in the affected part in the depth direction thereof becomes undulated as shown in FIG. 9.

The distribution of radiation dose in the body in the case where the Bragg peak enlarging device 17 is disposed in the front of the ridge filter 24 in the first embodiment will be described below. An ion beam advances from the filter element 18 to the filter element 21. The ion beam that has passed through the Bragg peak enlarging device 17, as described above, contains the three ion beam components having different energies. Accordingly, the width of each Bragg peak formed in the body by irradiation with the ion beam that has passed through the ridge filter 24 becomes large. In the first embodiment, the number of the steps 34 of the ridge filter 24 is reduced to 2/3 compared to the related art in which the Bragg peak enlarging device 17 is not disposed. Accordingly, the manufacture of the ridge filter 24 becomes easy, and the time required to manufacture the ridge filter 24 can be shortened. The width of each Bragg peak formed in the body becomes large owing to the disposition of the Bragg peak enlarging device 17, whereby even if the ridge filter 24 having the reduced number of steps 34 is used, the radiation dose in the depth direction becomes uniform as shown by the line 35 in FIG. 8.

The ion beam that has passed through the ridge filter 24 passes through the range shifter 25 and is irradiated onto an affected part 32 through the collimator 26 and the bolus 27. The collimator 26 cuts the enlarged ion beam according to the horizontal shape of the affected part 32 of the patient 31 lying on a treatment table 30. The bolus 27 adjusts the energy of the ion beam cut by the collimator 26, according to the maximum depth of the affected part 32 from the body surface of the patient 31. In the first embodiment, the total radiation dose in the body in the case of irradiation with the ion beam becomes as shown by the line 35 in FIG. 8.

In the first embodiment, the width of a Bragg peak can be made large owing to the disposition of the Bragg peak enlarging device 17. Accordingly, the width of each Bragg peak formed by the ridge filter 24 becomes large, and the total radiation dose distribution formed in the body becomes uniform. In the first embodiment in particular, the filter element 18 and the filter element 21 are disposed so that the respective stick-shaped portions 19 and 22 are partly superposed on each other in the advancing direction of an ion beam, i.e., mutually intersect, whereby it is possible to obtain ion beam components having different energies (refer to FIG. 4), the number (three) of which is larger than the number (two) of the stick-shaped portions superposed on each other in the advancing direction of the ion beam. It is also possible to increase the width in the depth direction of the Bragg peak formed in the body by the irradiation of the patient 31 with the ion beam having the three ion beam components. In the first embodiment, it is possible to obtain far more ion beam components having different energies by means of a simple construction in which fewer stick-shaped portions are disposed in the advancing direction of the ion beam, whereby it is possible to increase the width of the Bragg peak in the depth direction.

In the first embodiment, the Bragg peak enlarging device 17 can easily obtain an ion beam having three ion beam components having different energies, merely by making the direction of stick-shaped portions, i.e., thick-walled portions, in one filter element different from that in another among a plurality of filter elements. Even if there occurs a deviation of a position where the thick-walled portions of both filter elements are superposed with their directions made mutually different, or even if the directions of the thick-walled portions are mutually deviated to a small extent, the energy of each of the three ion beam components remains unchanged, and the proportion of the three ion beam components does not change very much. In addition, even with another example of the Bragg peak enlarging device which will be described later, it is possible to obtain the advantage obtained with the disposition of the Bragg peak enlarging device 17.

Figure 10A:
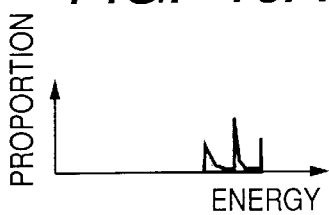
FIG. 10A shows an explanatory view of the energy distribution of an ion beam that has passed through a ridge filter having stick-shaped portions with circular longitudinal sectional shapes.
Figure 10B:
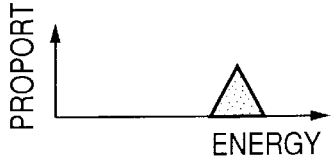
FIG. 10B shows an explanatory view of the energy distribution of an ion beam that has passed through a ridge filter having stick-shaped portions with triangular longitudinal sectional shapes.

The cross-sectional shape of each of the stick-shaped portions 19 and 22 of the filter elements 18 and 21 may be circular or triangular. In the case where a Bragg peak enlarging device is used in which two filter elements each having a plurality of stick-shaped portions whose cross-sectional shapes are circular are disposed so that their stick-shaped portions intersect as viewed from above, an ion beam that has passed through the Bragg peak enlarging device contains ion beam components having different energies as shown in FIG. 10A. In the case where a Bragg peak enlarging device is used in which two filter elements each having a plurality of stick-shaped portions whose cross-sectional shapes are triangular are disposed so that their stick-shaped portions intersect as viewed from above, an ion beam that has passed through the Bragg peak enlarging device contains ion beam components having different energies as shown in FIG. 10B.

Figure 11:
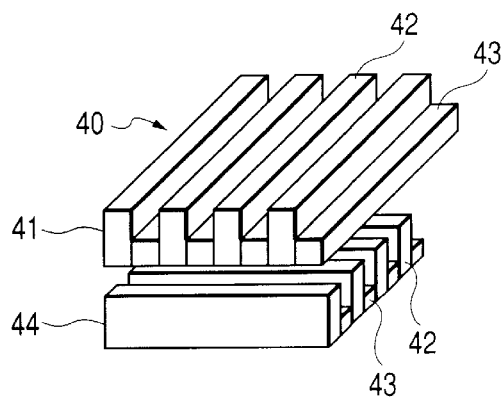
FIG. 11 is a perspective view of another example of the Bragg peak enlarging device.

Another example of the Bragg peak enlarging device 17 will be described below with reference to FIG. 11. A Bragg peak enlarging device 40 has a pair of filter elements 41 and 44. The filter element 41 is disposed over the filter element 44. The filter element 41 includes stick-shaped portions 42 and 43 which are alternately disposed and joined together. The cross-sectional shape of each of the stick-shaped portions 42 is rectangular, and the thickness of the stick-shaped portions 42 in the advancing direction of an ion beam is larger than the thickness of the stick-shaped portions 43 in the same direction. The stick-shaped portions 42 are made of a material containing an element having a small atomic number, while the stick-shaped portions 43 are made of a material containing an element having a large atomic number. The filter element 44 also has the same construction as the filter element 41. The filter element 41 and the filter element 44 are disposed with their stick-shaped portions 42 and 43 arranged in mutually different directions (for example, in such a manner as to cross at right angles as viewed from above). An ion beam passes through the filter elements 41 and 44 from above. The ion beam is decreased in energy and is scattered by passing through the two filter elements 41 and 44. In general, a material containing an element having a larger atomic number is larger in the extent of energy decrease and in the extent of scattering as the thickness of the material through an ion beam is to pass is larger. In the Bragg peak enlarging device 40, by appropriately selecting the thickness of each of the two kinds of stick-shaped portions 42 and 43 as well as the atomic numbers of elements constituting the respective two kinds, an ion beam which has passed through the Bragg peak enlarging device 40 can be formed to exhibit an energy distribution similar to that of an ion beam which has passed through the Bragg peak enlarging device 17 shown in FIG. 3, and in addition, the extent of scattering of the ion beam can be made uniform.

Figure 13:
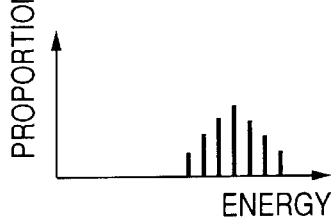
FIG. 13 is an explanatory view of the energy distribution of an ion beam that has passed through the Bragg peak enlarging device shown in FIG. 12.
Figure 12:
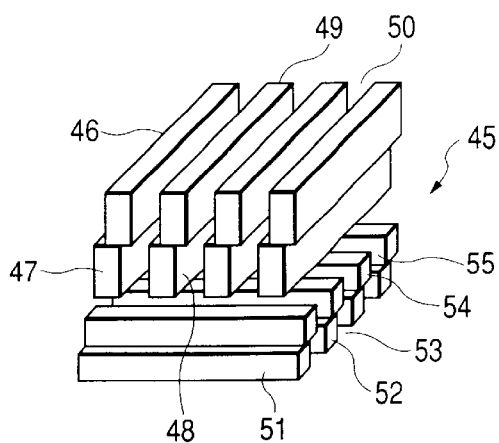
FIG. 12 is a perspective view of another example of the Bragg peak enlarging device.

Another example of the Bragg peak enlarging device will be described below with reference to FIG. 12. A Bragg peak enlarging device 45 has a pair of filter elements 46 and 51 which are disposed in the vertical direction. The filter element 46 has a construction in which a plurality of stick-shaped portions 47 are disposed on a lower side in an equally spaced manner, while a plurality of stick-shaped portions 49 are disposed on an upper side in an equally spaced manner. Although not shown, the stick-shaped portions 47 and 49 are connected to one another at their opposite ends similarly to those in the filter element 18. The stick-shaped portions 49 are disposed to be horizontally displaced so that they are partly superposed on the stick-shaped portions 47. Hole portions 48 are formed between the respective stick-shaped portions 47, and hole portions 50 are formed between the respective stick-shaped portions 49. The hole portions 48 and the hole portions 50 are horizontally displaced from each other, but the hole portions 48 communicate with the hole portions 50, respectively. The cross-sectional shape of each of the stick-shaped portions 47 and 49 is rectangular. The filter element 51 similarly has a construction in which a plurality of stick-shaped portions 52 are disposed on a lower side in an equally spaced manner, while a plurality of stick-shaped portions 54 are disposed on an upper side in an equally spaced manner, and the stick-shaped portions 52 and 54 are connected to one another at their opposite ends. The stick-shaped portions 54 are disposed to be horizontally displaced so that they are partly superposed on the stick-shaped portions 52. Hole portions 53 are formed between the respective stick-shaped portions 52, and hole portions 55 are formed between the respective stick-shaped portions 54. The hole portions 53 and the hole portions 55 are horizontally displaced from each other, but the hole portions 53 communicate with the hole portions 55, respectively. The cross-sectional shape of each of the stick-shaped portions 47 and 49 is square. The thickness in the height direction of each of the stick-shaped portions 47 and 49 is twice as large as that of each of the stick-shaped portions 52 and 54. In the Bragg peak enlarging device 45, the stick-shaped portions 47 and 49 of the filter element 46 are disposed to extend in a direction different from the stick-shaped portions 52 and 54 of the filter element 51, and the filter element 46 is disposed over the filter element 51. An ion beam that has passed through the Bragg peak enlarging device 45 contains seven ion beam components having different energies as shown in FIG. 13, such as an ion beam component that has passed through all the four stick-shaped portions 47, 49, 52 and 54 and an ion beam component that has passed through the holes 50 and 48 without passing through any of the stick-shaped portions. Because the ion beam contains such seven ion beam components, the Bragg peak enlarging device 45 can form a finer energy distribution than can the Bragg peak enlarging devices 17 and 40. The Bragg peak enlarging device 45 can also be applied to a case where the energy of an injected ion beam is low and a Bragg peak is thin.

Figure 14:
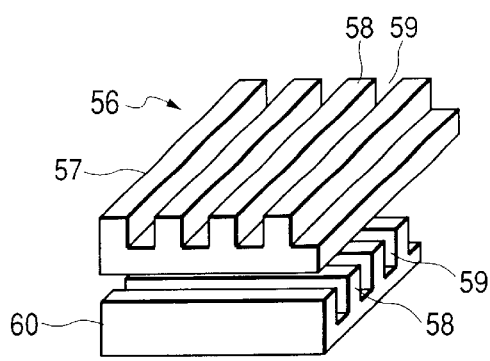
FIG. 14 is a perspective view of another example of the Bragg peak enlarging device.

Another example of the Bragg peak enlarging device will be described with reference to FIG. 14. A Bragg peak enlarging device 56 has a pair of filter elements 57 and 60. The filter element 57 has the same shape as the filter element 41. The filter element 57 includes one plate in which a plurality of groove portions 59 are formed to form a plurality of convex portions 58. The convex portions 58 are thick-walled portions, and each of the convex portions 58 extends in one direction. The filter element 60 also includes a plurality of groove portions 59 and a plurality of convex portions 58 which extend in one direction. In the Bragg peak enlarging device 56, the convex portions 58 of the filter element 57 and the convex portions 58 of the filter element 60 are disposed to extend in mutually different directions, and the filter element 57 is disposed over the filter element 60. The Bragg peak enlarging device 56 also generates three ion beam components similarly to the Bragg peak enlarging device 17, thereby increasing the width of a Bragg peak.

Incidentally, although the irradiation field forming device 13 shown in FIG. 2 uses a ridge filter, a range modulating propeller may also be used instead of a ridge filter.

In the first embodiment, a beam enlarging device may also be used in which scatters are disposed instead of the electromagnets 14 and 15 in the construction of the beam enlarging device 16. Namely, the beam enlarging device has a construction in which two scatters are disposed in series with the advancing direction of an ion beam. An ion beam injected into the beam enlarging device is enlarged by the two scatters in a direction which intersects the advancing direction.

Embodiment 2

Figure 15:
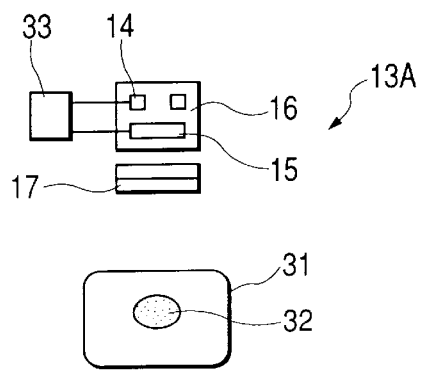
FIG. 15 is a diagrammatic view of the construction of the irradiation field forming device of a charged particle beam irradiation apparatus according to another preferred embodiment of the invention.

A charged particle beam irradiation apparatus according to a second preferred embodiment of the invention will be described below. The charged particle beam irradiation apparatus according to the second preferred embodiment has a construction in which the irradiation field forming device 13 of the charged particle beam irradiation apparatus 1 shown in FIG. 1 is replaced with the irradiation field forming device 13A shown in FIG. 15. The other construction of the charged particle beam irradiation apparatus according to the second preferred embodiment is the same as that of the charged particle beam irradiation apparatus 1. The irradiation field forming device 13A includes a casing in which a beam deflecting device 61 having the pair of scanning electromagnets 14 and 15 and the Bragg peak enlarging device 17 are disposed as shown in FIG. 15. The power source unit 33 is connected to the scanning electromagnets 14 and 15. In the second embodiment, the scanning electromagnets 14 and 15 function as a charged particle beam scanning device which scans the ion beam in the horizontal plane. Unlike the beam enlarging device 16, the beam deflecting device 61 is incapable of enlarging an ion beam in a direction perpendicular to the direction of injection of the ion beam into the beam deflecting device 61.

The ion beam ejected from the synchrotron 4 reaches the irradiation field forming device 13A via the beam transportation line 9. The synchrotron 4 generates an ion beam which is small in diameter compared to the affected part 32. When currents are caused to flow into the respective scanning electromagnets 14 and 15 from the power source unit 33, the beam deflecting device 61 scans the ion beam in a direction perpendicular to the direction of injection of the ion beam into the irradiation field forming device 13A. The ion beam can be scanned on the patient 32 by this scanning. The ion beam deflected is guided to the Bragg peak enlarging device 17 and passes through the Bragg peak enlarging device 17. The ion beam that has passed through the Bragg peak enlarging device 17 contains three ion beam components having different energies similarly to the case of the first embodiment. The width of a Bragg peak can be increased by irradiating the affected part 32 with the ion beam containing three ion beam components having different energies. By generating a plurality of ion beams having different energies through the synchrotron 4, it is possible to divide the affected part 32 into a plurality of areas in the depth direction thereof and irradiate the ion beam onto each divided area of the affected part 32 by scanning.

Specifically, the amount of scanning of the ion beam by the beam deflecting device 61 is controlled on the basis of preset scanning pattern data. A particular irradiation target layer of the affected part 32 in the depth direction thereof is irradiated with the ion beam while the ion beam is being scanned on the basis of the corresponding scanning pattern data. On completion of the irradiation of the irradiation target layer, the ejection of the ion beam from the synchrotron 4 is brought to a stop, and preparations for effecting irradiation of an ion beam onto a different irradiation target layer present at a shallower position are made. Specifically, the setting parameters of the synchrotron 4 are changed so that an ion beam having a different energy is generated, and the scanning pattern data for the beam deflecting device 61 is also set to pattern data corresponding to the different irradiation target layer. After that, an ion beam having a predetermined energy is ejected from the synchrotron 4, and the ion beam is irradiated onto the different irradiation target layer of the affected part 32 from the irradiation field forming device 13A. This irradiation is repeated to irradiate the whole of the affected part 32 with ion beams.

Figure 16:
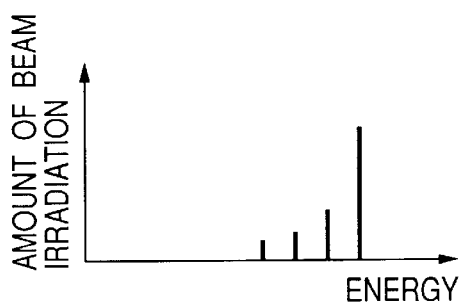
FIG. 16 is an explanatory view of the relationship between the energy of an ion beam supplied from the synchrotron of the charged particle beam irradiation apparatus according to the embodiment shown in FIG. 15 and the proportion of irradiation doses onto the affected part.
Figure 17:
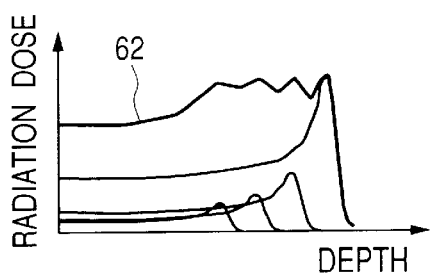
FIG. 17 is an explanatory view showing the distribution of radiation dose in the affected part in a case where the Bragg peak enlarging device is not disposed.

A description will be given in connection with a case where four ion beams having different energies as shown in FIG. 16 are sequentially irradiated onto irradiation target layers of the affected part 32 from the synchrotron 4 with the respective irradiation doses shown in FIG. 16 without the use of the Bragg peak enlarging device 17. In this case, the total radiation dose applied to the entire affected part 32 is as shown by a line 62 in FIG. 17. The four thin lines shown in FIG. 17 represent Bragg peaks formed by the ion beams irradiated onto the respective irradiation target layers. The line 62 represent the total radiation dose distribution obtained by adding the Bragg peaks together. Since the interval between each of the Bragg peaks is wide compared to the thinness thereof, the total radiation dose distribution is uniform in the depth direction. To solve this problem, consideration may be given to the method of uniformizing the total radiation dose distribution by increasing the number of ion beams having different energies to be generated by the synchrotron 4. However, if the number of ion beams having different energies is increased, the number of irradiation target layers increases in the depth direction, so that the irradiation time of ion beams increases.

Figure 18:
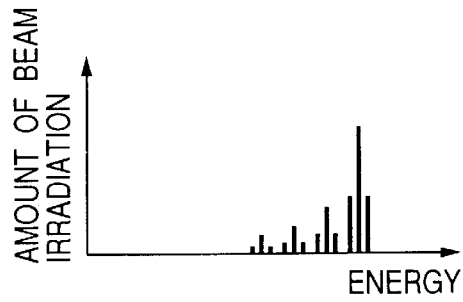
FIG. 18 is an explanatory view showing the energy distribution of an ion beam irradiated onto the affected part in a case where the Bragg peak enlarging device is disposed.
Figure 19:
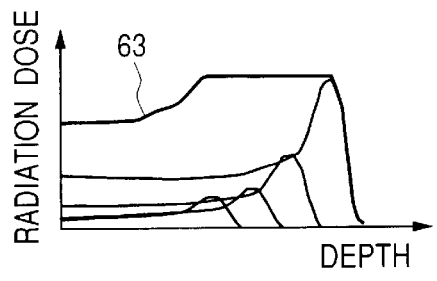
FIG. 19 is an explanatory view showing the distribution of radiation dose in the affected part in a case where the Bragg peak enlarging device is disposed.

On the other hand, in the second embodiment in which the Bragg peak enlarging device 17 is disposed, each of the four ion beams having different energies as shown in FIG. 16 contains three ion beam components having different energies as shown in FIG. 18. Accordingly, when the affected part 32 is irradiated with the ion beams having such different energies, the widths of Bragg peaks formed by the respective ion beams increase as shown by thin lines in FIG. 19. Accordingly, the total radiation dose distribution obtained by adding the Bragg peaks together becomes uniform in the depth direction of the affected part 32 as shown by a line 63 in FIG. 19.

In the second embodiment, because the widths of the respective Bragg peaks can be increased owing to the disposition of the Bragg peak enlarging device 17, it is possible to make far more uniform the total radiation dose in the depth direction of the affected part 32 without increasing the number of ion beams having different energies in the synchrotron 4. Because the widths of the respective Bragg peaks can be increased, the thickness of each irradiation target layer set in the depth direction can be increased, and the time required to irradiate the affected part 32 can be shortened. Even in the second embodiment, since the filter elements 18 and 21 are disposed, it is possible to obtain the effect and advantage obtained in the first embodiment.

Any of the Bragg peak enlarging devices 40, 45 and 56 may also be used instead of the Bragg peak enlarging device 17. In particular, by using the Bragg peak enlarging device 40, it is possible to adjust uniformly the extent of scattering of ion beams while the ion beams are passing through the Bragg peak enlarging device 40. Accordingly, it is possible to easily control the diameters of the respective ion beams during the scanning of the ion beams.

Incidentally, in the second embodiment, the energy of an ion beam is changed for each irradiation target layer having a different depth, by changing the parameters of the charged particle beam generation device. However, the energy of an ion beam can also be changed by providing the irradiation field forming device 13A with a range shifter and changing the thickness of the range shifter.

Embodiment 3

Figure 20:
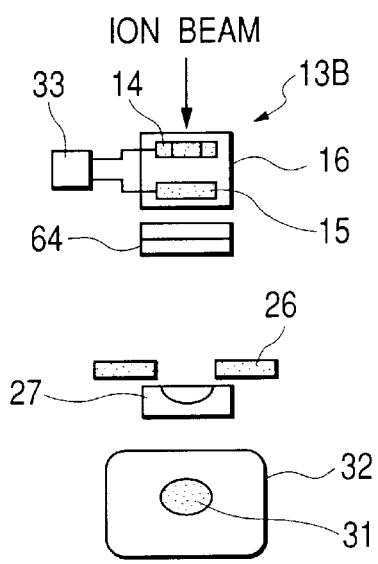
FIG. 20 is a view of the construction of an irradiation field forming device of a charged particle beam irradiation apparatus according to another embodiment of the invention.

A charged particle beam irradiation apparatus according to a third preferred embodiment of the invention will be described below. The charged particle beam irradiation apparatus according to the third preferred embodiment has a construction in which the irradiation field forming device 13 of the charged particle beam irradiation apparatus 1 shown in FIG. 1 is replaced with the irradiation field forming device 13B shown in FIG. 20. The other construction of the charged particle beam irradiation apparatus according to the third preferred embodiment is the same as that of the charged particle beam irradiation apparatus 1. The irradiation field forming device 13B includes the beam enlarging device 16 and a Bragg peak enlarging device 64, and the collimator 26 and the bolus 27 can be disposed. The irradiation field forming device 13A of the second embodiment is capable of effecting irradiation with scanning ion beams in different irradiation target layers of the affected part 32 in the depth direction thereof. The irradiation field forming device 13B used in the third embodiment irradiates the respective irradiation target layers with different ion beams enlarged by the beam enlarging device 16.

Figure 21:
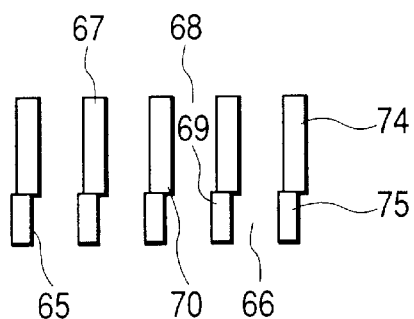
FIG. 21 is a longitudinal sectional view of the Bragg peak enlarging device shown in FIG. 20.

As shown in FIG. 21, the Bragg peak enlarging device 64 has a pair of filter elements 75 and 74. The filter element 75 is disposed on a lower side and has a construction in which a plurality of stick-shaped portions 65 are disposed to form hole portions 66 thereamong, while the filter element 74 is disposed on an upper side and has a construction in which a plurality of stick-shaped portions 67 are disposed to form hole portions 68 thereamong. The stick-shaped portions 65 and 67 are disposed to extend in the same direction. The stick-shaped portions 67 are disposed to be partly superposed on the respective stick-shaped portions 65 in the longitudinal directions thereof. The arrangement pitch of the stick-shaped portions 67 is the same as that of the stick-shaped portions 65. Therefore, the widths of the respective hole portions 66 are the same as those of the respective hole portions 68. Although not shown, the stick-shaped portions 65 are connected to one another at their opposite ends, and the stick-shaped portions 67 are connected to one another at their opposite ends. The thickness of each of the stick-shaped portions 67 in the height direction thereof is twice as large as that of each of the stick-shaped portions 65. Since the respective stick-shaped portions 67 are disposed to be partly superposed on the stick-shaped portions 65 as described above, steps 69 are formed on the top ends of the respective stick-shaped portions 65, while steps 70 are formed on the bottom ends of the respective stick-shaped portions 67. Each of the steps 70 covers a portion of a respective one of the hole portions 66.

Figure 22:
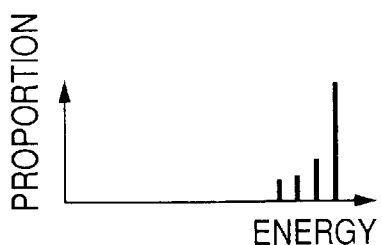
FIG. 22 is an explanatory view showing the energy distribution of an ion beam that has passed through the Bragg peak enlarging device shown in FIG. 21.

An ion beam that has passed through the Bragg peak enlarging device 64 contains four ion beams having different energies as shown in FIG. 22. An ion beam component that has passed through both stick-shaped portions 65 and 67 is the smallest in energy. An ion beam component that has passed through both hole portions 66 and 68 is the highest in energy.

Figure 23:
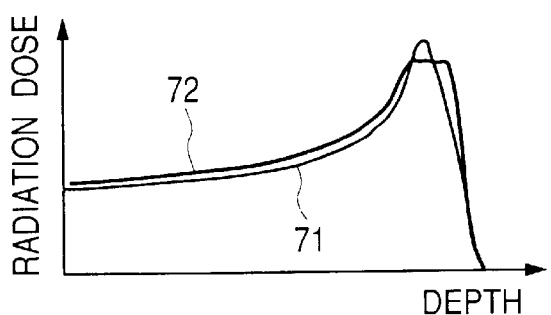
FIG. 23 is an explanatory view showing the distribution of radiation dose in the affected part at the time of irradiation with the ion beam that has passed through the Bragg peak enlarging device.

In the Bragg peak enlarging device 64, a Bragg peak having a different width is formed according to the width of a portion where one of the stick-shaped portion 65 and the adjacent one of the stick-shaped portion 67 are superposed on each other. Specifically, if the superposed portion between one of the stick-shaped portion 65 and the adjacent one of the stick-shaped portion 67 is small in width, the width of the Bragg peak does not increase, as shown by a line 71 in FIG. 23. If the superposed portion between one of the stick-shaped portion 65 and the adjacent one of the stick-shaped portion 67 has a width larger than a certain extent, the width of the Bragg increases, as shown by a line 72 in FIG. 23. In the Bragg peak enlarging device 64 used in the third embodiment, the stick-shaped portions 65 and the stick-shaped portions 67 are superposed on one another so that a Bragg peak such as that shown by the line 72 is formed.

The ion beam that has passed through the Bragg peak enlarging device 64 and contains the four ion beam components having different energies is irradiated onto an irradiation target layer located at the deepest position in the affected part 32, through the collimator 26 and the bolus 27. Then, an ion beam which is decreased in energy by the manipulation of the synchrotron 4 is ejected from the synchrotron 4. This ion beam is irradiated onto another irradiation target layer located immediately above the irradiation target layer irradiated previously. The ion beam also contains four different ion beam components having different energies. In this manner, an ion beam is sequentially irradiated onto each overlying irradiation target layer. In the third embodiment, four irradiation target layers are set in the affected part 32 in the depth direction thereof, and the respective irradiation target layers are irradiated with the ion beams that have passed through the Bragg peak enlarging device 64.

In the third embodiment, the filter element 74 and filter element 75 are disposed so that the respective stick-shaped portions 67 and 65 are partly superposed on each other in the advancing direction of an ion beam, whereby it is possible to obtain ion beam components having different energies (refer to FIG. 22), the number (four) of which is larger than the number (two) of the stick-shaped portions superposed on each other in the advancing direction of the ion beam. It is also possible to increase the width in the depth direction of the Bragg peak formed in the body by the irradiation of the patient 31 with the ion beam having the four ion beam components. In the third embodiment as well, it is possible to obtain far more ion beam components having different energies by means of a simple construction in which fewer stick-shaped portions are disposed in the advancing direction of the ion beam, whereby it is possible to increase the width of the Bragg peak in the depth direction.

In the third embodiment, because the Bragg peak enlarging device 64 is disposed, the width of the Bragg peak increases, and the thickness of each irradiation target layer can be made large in the depth direction. Accordingly, it is possible to shorten the time required to irradiate the affected part 32. However, the Bragg peak enlarging device 64 needs complicated work in the adjustment of the width of each of the superposed portions between the stick-shaped portions 65 and 67.

In each of the above-described embodiments, a cyclotron can be used instead of a synchrotron. The beam enlarging device 16 and the beam deflecting device 61 are ion beam scanning devices.

According to the invention, the width in the depth direction of a Bragg peak formed in the body by irradiation with a charged particle beam can be increased by a simple construction.

What is claimed is:

1. A charged particle beam irradiation apparatus comprising:
   a charged particle beam generation device including an accelerator; and
   an irradiation device for irradiating an irradiation target portion with a charged particle beam generated from the charged particle beam generation device;
   the irradiation device having a charged particle beam scanning device for scanning the charged particle beam and a Bragg peak enlarging device for increasing a width in a depth direction of a Bragg peak formed by the charged particle beam scanned by the charged particle beam scanning device,
   the Bragg peak enlarging device having a first filter member and a second filter member which are disposed in order in an advancing direction of the charged particle beam and each of which has at least one thick-walled portion in a direction intersecting the advancing direction,
   the first filter member and the second filter member being disposed with their respective thick-walled portions intersecting mutually in the advancing direction of the charged particle beam.

2. A charged particle beam irradiation apparatus according to claim 1, wherein each of the first filter member and the second filter member has a plurality of stick-shaped portions which are the thick-walled portions, the plurality of stick-shaped portions being spaced apart from one another in each of the first filter member and the second filter member, the first filter member and the second filter member being disposed with their plurality of stick-shaped portions arranged in mutually different directions.

3. A charged particle beam irradiation apparatus according to claim 2, wherein the plurality of stick-shaped portions include a plurality of stick-shaped portions made of different materials.

4. A charged particle beam irradiation apparatus according to claim 1, wherein each of the first filter member and the second filter member has a plurality of thick-walled portions extending in one direction and a plurality of thin-walled portions respectively disposed between the plurality of thick-walled portions and smaller in thickness than the plurality of thick-walled portions, the first filter member and the second filter member being disposed with their plurality of thick-walled portions arranged in mutually different directions.

5. A charged particle beam irradiation apparatus according to claim 1, wherein a ridge filter to which the charged particle beam that has passed through the Bragg peak enlarging device is to be guided is disposed in one of the front and the rear of the Bragg peak enlarging device.

6. A charged particle beam irradiation apparatus according to claim 1, wherein the direction intersecting the advancing direction is a direction perpendicular to the advancing direction.

7. A charged particle beam irradiation apparatus comprising:
   a charged particle beam generation device including an accelerator; and
   an irradiation device for irradiating an irradiation target portion with a charged particle beam generated from the charged particle beam generation device;
   the irradiation device having a charged particle beam scanning device for scanning the charged particle beam and a Bragg peak enlarging device for increasing a width in a depth direction of a Bragg peak formed by the charged particle beam scanned by the charged particle beam scanning device,
   the Bragg peak enlarging device having a first filter member and a second filter member which are disposed in order in an advancing direction of the charged particle beam and each of which has at least one thick-walled portion in a direction intersecting the advancing direction, the at least one thick-walled portion of the first filter member being different in thickness in the advancing direction from the at least one thick-walled portion of the second filter member,
   the first filter member and the second filter member being disposed with their respective thick-walled portions partly intersecting mutually in the advancing direction of the charged particle beam.

8. A charged particle beam irradiation apparatus according to claim 3, wherein the direction intersecting the advancing direction is a direction perpendicular to the advancing direction.

9. A charged particle beam irradiation apparatus comprising:
   a charged particle beam generation device including an accelerator; and
   an irradiation device for irradiating an irradiation target portion with a charged particle beam generated from the charged particle beam generation device;
   the irradiation device having a scatter for enlarging the charged particle beam in a direction intersecting an advancing direction of the charged particle beam, and a Bragg peak enlarging device for increasing a width in a depth direction of a Bragg peak formed by the charged particle beam that has passed through the scatter,
   the Bragg peak enlarging device having a first filter member and a second filter member which are disposed in order in the advancing direction of the charged particle beam and each of which has at least one thick-walled portion in the direction intersecting the advancing direction,
   the first filter member and the second filter member being disposed with their respective thick-walled portions partly intersecting mutually in the advancing direction of the charged particle beam.

10. A charged particle beam irradiation apparatus according to claim 9, wherein each of the first filter member and the second filter member has a plurality of stick-shaped portions which are the thick-walled portions, the plurality of stick-shaped portions being spaced apart from one another in each of the first filter member and the second filter member, the first filter member and the second filter member being disposed with their plurality of stick-shaped portions arranged in mutually different directions.

11. A charged particle beam irradiation apparatus according to claim 10, wherein the plurality of stick-shaped portions include a plurality of stick-shaped portions made of different materials.

12. A charged particle beam irradiation apparatus according to claim 9, wherein the direction intersecting the advancing direction is a direction perpendicular to the advancing direction.

13. A charged particle beam irradiation apparatus according to claim 4, wherein a ridge filter to which the charged particle beam that has passed through the Bragg peak enlarging device is to be guided is disposed in one of the front and the rear of the Bragg peak enlarging device.

* * * * *